United States Patent [19]

Farkas et al.

[11] Patent Number: 4,488,901
[45] Date of Patent: Dec. 18, 1984

[54] COMPOSITIONS FOR INCREASING THE COLD RESISTANCE OF CULTIVATED PLANTS AND A METHOD FOR THE UTILIZATION OF SUCH COMPOSITIONS

[75] Inventors: Tibor Farkas; Ibolya Horvath; Laszlo I. Horvath; Laszlo Vigh, all of Szeged; Zsolt Dombay; Jozsef Nagy, both of Miskolc; Emilia Nagy née Gera; Csaba Pavliscsak, both of Sajobabony; Gyula Tarpai, Miskolc, all of Hungary

[73] Assignee: Északmagyarországi Vegyimüvek, Gyártelep, Hungary

[21] Appl. No.: 331,921

[22] Filed: Dec. 17, 1981

[30] Foreign Application Priority Data

Dec. 18, 1980 [HU] Hungary ............................... 3036/80

[51] Int. Cl.³ .............................................. A01N 33/02
[52] U.S. Cl. ........................................................ 71/121
[58] Field of Search ........................................ 71/121

[56] References Cited

U.S. PATENT DOCUMENTS 4,311,517 1/1982 Youngmann et al. ................. 71/121

OTHER PUBLICATIONS

The Merk Index, 9th Edition, (1976), pp. 490–3654 and 285–2201.
French Pat. 1,441,422, Chem. Abst., vol. 66, (1967), 27943j.
Kamalyan et al., Chem. Abst., vol. 77, (1972), 44182e.
Rambhav et al., Chem. Abst., vol. 84, (1976), 31470s.
Horvath et al., Chem. Abst., vol. 94, (1981), 100009a.
Article entitled "Effect of Chloine Chloride on Fatty Acid Chain Ordering in Membranes of Wheat", by I. Horvath et al, pp. 476–480.
Article entitled "The Manipulation of Polar Head Group Composition of Phospholipids in the Wheat Miranovskaja 808 Affects Frost Tolerance", by I. Horvath et al., pp. 103–108, (1981).

*Primary Examiner*—Catherine L. Mills
*Attorney, Agent, or Firm*—Karl F. Ross

[57] ABSTRACT

The invention relates to new compositions for increasing the cold resistance of cultivated plants. These compositions contain as active ingredient at least one compound of the general formula (I),

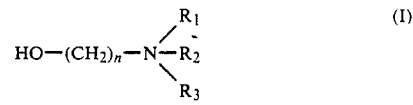

wherein n is an integer of 2 to 5 and $R_1$, $R_2$ and $R_3$ each stand for hydrogen or $C_{1-5}$ alkyl, or an acid addition salt thereof in an amount of 0.01 to 70% by weight, together with a conventional diluent and/or additive.

The plants treated with the compositions according to the invention are more resistant to cold and frost.

9 Claims, No Drawings

COMPOSITIONS FOR INCREASING THE COLD RESISTANCE OF CULTIVATED PLANTS AND A METHOD FOR THE UTILIZATION OF SUCH COMPOSITIONS

The invention relates to compositions for increasing the cold resistance of cultivated plants, as well as to an agricultural method for the utilization of such compositions.

The compositions according to the invention comprise as active ingredient one or more compounds of the formula (I),

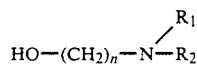

wherein n is an integer of 2 to 5 and $R_1$ and $R_2$ each stand for hydrogen or $C_{1-5}$ alkyl, or quaternary ammonium salts thereof in an amount of 0.01 to 70% by weight, together with 30 to 95% by weight of one or more solid and/or liquid diluents and 0.1 to 15% by weight of one or more surfactants and/or additives.

It is well known that climatic conditions, primarily the temperature of the environment, play a decisive role in the diversity of the geographic distribution of plants. This temperature-caused selection is of primary importance with respect to cereals, vegetables and fruits indispensable for food. Agrotechnicians dealing with cultivation and improvement in countries of continental climate, such as in Hungary, must accurately know the limit of cold and frost resistance of all cultivated plants. Of course, substantial frost damage cannot be avoided even having the necessary resistance data.

There are three ways for decreasing the apparently unavoidable risks. The most ancient method of preventing frost damages is fumigation or, as a more developed variant, the use of fog candles. The aim of this treatment is to provide an air temperature above freezing point in the surroundings of the plants exposed to frost damage and to prevent cold air from reaching the plants. This method is difficult to perform and cannot be applied to all cultures (e.g. on flowering fruit trees). As an additional disadvantage, the smoke or fog should be maintained continuously until the risk of frost damage exists, which is a difficult task particularly under windy weather conditions. The second possibility for preventing frost damage, far more significant than the above, is the development of new, cold-resistant varieties with appropriate crop yields. This requires, however, lengthy and expensive research work, furthermore it cannot be applied for all plant varieties, since in plant cultivation one property can be improved most frequently at the expense of another. With some cultivated plants the extent of frost sensitivity is so high that an improvement in development of resistant species appears to be hopeless.

The third possibility of preventing frost damages is the use of protective chemicals, based on an extensive study of the damaging of plants and parts thereof upon freezing and the investigation of the biochemical mechanisms of such freezing processes [Ilker, R., Warring, A. J., Lyons, J. M., Breidenbach, R. W.: The cytological responses of tomato seedling cotyledons to chilling and the influence of membrane modifications upon these responses; Protoplasma 90, 90–96 (1976)].

As a result of these investigations it has become generally acknowledged that the membranes of plant cells and cell components, and of the membrane components primarily the lipoids, have a cardinal role in the occurrence of frost resistance. This, in a simplified approach, can be related to the phase transition temperatures of lipoids. When the temperature is below critical (or below a critical range for mixtures of lipoids), the membrane lipoids convert from the physiological liquid-crystalline state into the so-called solid-gel state. In this solid-gel state all functions of the membranes (e.g. the activity of the enzymes bound to the membrane, the semipermeability of the membrane, the progress of transport processes, etc.) are irreversibly damaged. Moreover, at temperatures below 0° C. another important factor, the water/ice phase transition has adverse effects, too. Water in the tissues freezes in the intercellular spaces first, which, in most instances, is still insufficient to destroy the plant. Plants are destroyed when freezing extends to the intracellular space, too, since under such conditions the proteins and other macromolecules also lose the bound water indispensable for maintaining their native conformation. Freezing, involving an expansion in volume, causes mechanical damage as well, sufficient to kill the plant.

It follows from the above mechanism that a decisive factor of survival is to prevent the plants from intracellular freezing, or at least to delay this process.

Intracellular freezing can be delayed, in principle, in several ways, such as by slowing down the rate of cooling (more particularly, creating conditions which slow down the rate of cooling), optional overcooling (in which water-soluble cryoprotective substances might play a role), increasing the molar concentration of cell sap, or developing a cell membrane structure with an increased water permeability at low temperatures.

Probably, almost all of the above factors can be influenced chemically, which may be the third way of prevention.

When examining the cold resistance of plants we have found that the phase transition temperatures of membrane lipoids, their permeability and functions are determined by three basic factors:

the chain length and saturation degree of fatty acids present in lipoids as esterifying components for glycerol, the appearance of cryoprotective substances at low temperatures which influence the fluidity and water permeability of membranes, and the quality of the individual lipoids, the ratio of lipoids with different "head groups" in the membrane structures, and their interactions with other cell compounds.

From the experimental results we arrived at the conclusion that the actual physico-chemical state of membrane lipoids is of decisive importance with respect to the evolution of an ability to resist cold, and when cold resistance is intended to be increased by chemical treatment, this should be directed to the modification of the lipoid composition.

One of the possible chemical treatments may be the introduction of complete lipoid molecules into the plant, which is, however, difficult to perform for solubility and permeability reasons. Another possibility may be the use of regulators which shift the lipoid household of the plant to the desired direction. These substances are, however, very expensive, applied only in laboratory-scale tests, and are not available for large-scale plant cultivation.

Our aim was to develop compositions which can be used for preventing cold-sensitive cultivated plants (e.g. vegetables, fruit trees, ornamental plants, flower plants, etc.) from damaging during the critical periods of temperature drop caused by climatic conditions, protecting thereby the cultivated plants and improving the security of cultivation.

It was an additional aim to elaborate methods of treatment using the compositions most effective in improving the cold resistance of plants.

As a result of our research work we have found that when plants are treated with the compositions according to the invention, the treatment results in a significant improvement in their cold resistance.

The compositions according to the invention contain as active ingredient one or more compounds of the formula (I), wherein n is an integer of 2 to 5 and $R_1$, $R_2$ and $R_3$ each stand for hydrogen or $C_{1-5}$ alkyl, or acid addition salts thereof in an amount of 0.01 to 70% by weight, together with 30 to 95% by weight of one or more solid and/or liquid diluents and 0.1 to 15% by weight of one or more surfactants and/or additives.

Compositions containing 2-hydroxyethylamine and-/or trimethyl-$\beta$-hydroxyethyl-ammonium chloride proved to be particularly effective in preventing plants from the damaging effects of temperature drop.

It has also been found that the treatment is the most effective when the cultivated plants to be protected are sprayed with a dilute aqueous mixture, containing 0.001 to 5.000% by weight of the active agents. However, other methods of treatment, such as dipping or soaking of grains or germs in a diluted solution of the composition, can sometimes be applied with good results, too.

It has been observed that the phase transition temperatures of membrane lipoids decrease substantially upon treating the plants with the compositions according to the invention, and a simultaneous significant increase occurs in the ratio of plants survived when exposed to low temperatures. This means that the ability of plants to resist cold improves significantly.

The invention is elucidated in detail by the aid of the following non-limiting Examples.

EXAMPLE 1

50 g of solid trimethyl-$\beta$-hydroxyethyl-ammonium chloride (choline chloride) are introduced into a round-bottomed flask, 250 ml in capacity, equipped with a stirrer, and than 5 g of a fatty acid-polyhydroxy ether, 1 g of a polyethyleneglycol fatty acid ester, 3 g of polyethylene glycol and 42 ml of distilled water are introduced in the given sequence. Stirring is started, and the mixture is stirred until all solids dissolve. The resulting liquid composition contains 50% by weight of the active agent of the formula (I).

EXAMPLE 2

10 g of trimethyl-$\beta$-hydroxyethyl-ammonium chloride are introduced into a round-bottomed flask, 250 ml in capacity, equipped with a stirrer, 10 g of ethylene glycol, 3 g of a fatty acid polyhydroxy ether and 1 g of a polyethyleneglycol fatty acid ester are added, and the volume of the mixture is adjusted to 100 ml with distilled water. Stirring is started, and the mixture is stirred until all solids dissolve. The resulting liquid composition contains 10% by weight of the active agent of the formula (I).

EXAMPLE 3

30 g of trimethyl-$\beta$-hydroxyethyl-ammonium chloride and 20 g of 2-hydroxyethylamine (ethanolamine) are introduced into a round-bottomed flask, 250 ml in capacity, equipped with a stirrer, 5 g of a fatty acid polyhydroxy ether, 1 g of a polyethyleneglycol fatty acid ester and 3 g of polyethylene glycol are added, and the volume of the mixture is adjusted to 100 ml with distilled water. Stirring is started, and the mixture is stirred until all solids dissolve. The resulting liquid composition contains as active agent a mixture of two compounds of the general formula (I) in an amount of 50% by weight.

EXAMPLE 4

30 g of trimethyl-$\beta$-hydroxyethyl-ammonium chloride and 30 g of 2-hydroxyethylamine are introduced into a round-bottomed flask, 250 ml in capacity, equipped with a stirrer, 1 g of a polyethyleneglycol fatty acid ester, 5 g of a fatty acid polyhydroxy ether and 3 g of polyethyleneglycol are added, and the volume of the mixture is adjusted to 100 ml with distilled water. Stirring is started, and the mixture is stirred for 0.5 hours. The resulting liquid composition contains as active agent a mixture of two compounds of the formula (I) in an amount of 60% by weight.

EXAMPLE 5

15 g of trimethyl-$\beta$-hydroxyethyl-ammonium chloride and 45 g of 2-hydroxyethylamine are introduced into a round-bottomed flask, 250 ml in capacity, equipped with a stirrer, 5 g of a fatty acid polyhydroxy ether, 1 g of a polyethyleneglycol fatty acid ester and 3 g of polyethyleneglycol are added, and the volume of the mixture is adjusted to 100 ml with distilled water. Stirring is started, and the mixture is stirred for 0.5 hours. The resulting liquid composition contains as active agent a mixture of two compounds of the formula (I) in an amount of 60% by weight.

EXAMPLE 6

0.1 g of trimethyl-$\beta$-hydroxyethyl-ammonium chloride, 0.2 g of a fatty acid polyhydroxy ether, 0.1 g of a polyethyleneglycol fatty acid ester and 10 g of polyethyleneglycol are introduced into a round-bottomed flask, 250 ml in capacity, equipped with a stirrer, and the volume of the mixture is adjusted to 100 ml with distilled water. Stirring is started, and the mixture is stirred for 0.5 hours. The resulting liquid composition contains the active agent of the formula (I) in a concentration of 0.1% by weight.

EXAMPLE 7

This example is to demonstrate that the composition of membrane lipoids changes in the plants treated with a composition according to the invention.

Wheat grains (Miranovskaya 808 variety) were pre-germinated on a wet filter paper at 25° C. for 2 days in the dark; then the grains were put on a gauze spanning a glass ring so that the germs extended vertically below the gauze. The rings were put into beakers, and the lower parts of the beakers were wrapped into black paper up to the height of the roots.

A serial aqueous dilution, containing 5, 15, 30 and 60 mmoles of the active agent of the formula (I), was prepared from the liquid composition described in Example 6. The aqueous solutions were poured below the pre-germinated grains so that the roots dipped into the solution. In the control test the beaker was filled with distilled water.

The seedlings were cultivated at 25° C. under illuminating them for 10 hours with an intensity of 8000 lux (daylight period) and keeping them then in the dark for 14 hours (night period). After 7 days of cultivation the leaves of the seedlings were prepared, the lipoids were extracted from the leaves, and the composition of the phospholipods was determined in three parallel samples by the method of Folch et al.

The major phospholipoids appearing in the leaves were the following: phosphatidic acid (PA), phosphatidylcholine (PC), phosphatidyl-inositol (PI), phosphatidyl-ethanolamine (PE), phosphatidyl-glyceride (PG) and phosphatidyl-glyceryl (DPG). The results of the measurements are listed in Table 1.

TABLE 1

| Active agent concentration mmoles | Distribution of phospholipoids, % | | | | |
|---|---|---|---|---|---|
| | PA | PC | PI | PE + PG | DPG |
| 5 | 28.4 | 28.1 | 9.2 | 25.6 | 7.6 |
| 15 | 27.6 | 29.9 | 10.3 | 24.7 | 7.5 |
| 30 | 24.0 | 31.4 | 9.9 | 28.1 | 6.5 |
| 60 | 19.6 | 42.4 | 9.3 | 21.3 | 7.4 |
| Untreated control | 30.6 | 24.2 | 9.2 | 27.6 | 8.3 |

It appears from the data of the table that among membrane phospholipoids the level of PC gradually increases in parallel with the incorporation of choline chloride; when a solution containing 60 mmoles of the active agent is applied, the level of PC is almost the double of that observed with the untreated control. Choline chloride, built into the cells, probably enters an addition reaction with PA to form PC; this is indicated by the gradual decrease in the level of PA. No significant change can be observed in the levels of other phospholipoids.

EXAMPLE 8

Tests were performed on wheat seedlings, prepared and cultivated as described in Example 7, to determine how the phase transition temperature range of membrane lipids and the temperature dependence of liquid-crystalline and solid-gel states are influenced upon treating the plants with a composition according to the invention.

Fey et al. [Fey, R. L., Warkman, M., Marcsilos, H., Burke, M. J.: Plant Physiol 63, 1220–1222 (1970)] elaborated an ESR method, examining the whole leaf, for the determination of phase transition temperature.

This method was modified by us as follows: 1 cm sections of wheat seedlings, cultivated as described in Example 11, were put into 3 ml of an aqueous solution of 2,2,6,6-tetramethyl-piperidine-oxyl (TEMPO) of 10 mmole concentration, and the test tubes were evacuated. After 10 minutes of infiltration, when the leaves became saturated with the solution of the compound containing free radicals, suction was stopped, the leaf surfaces were washed with distilled water, the leaves were subjected to vacuum treatment for 5 minutes, and then allowed to dry in the open air for 30 minutes.

The leaf segments were wrapped into paraffin foils, placed into the sample holder tube of the ESR spectrometer, and spectra were recorded in a temperature range of −20° C. to +25° C. The temperature dependence of the lipoid/water distribution coefficient was calculated from the spectra, and the starting and end values of the phase transition temperatures of the lipoids present in the untreated and treated leaves were determined from these data by a calculation not described in detail here. The results are listed in Table 2.

TABLE 2

| Active agent concentration mmoles | Phase transition temperature | |
|---|---|---|
| | Start, °C. | End, °C. |
| 5 | +20.3 | −2.5 |
| 15 | +7.3 | −8.5 |
| 30 | +2.0 | −9.0 |
| 60 | −5.0 | −9.0 |
| Untreated control | +23.5 | 0.0 |

It appears from the data of Table 2 that the transition temperatures of lipoids present in the treated leaves decrease drastically, which is the most important precondition of the improvement of cold resistance.

EXAMPLE 9

Tests were performed to determine how the treatments with the composition according to the invention influence the cold resistance of a frost-sensitive (Short Mexican) and a frost-resistant (Miranovskaya 808) wheat variety.

Seeds of the two wheat varieties were germinated for 48 hours on a wet filter paper at 5° C. in the dark. The germinating seeds were planted then at row distances of 10 cm into wooden cases, 25×50×10 cm in size, filled with a 2:1 mixture of soil and sand, and subjected to a "wintering program" with treatment conditions listed in Table 3.

TABLE 3

| Duration of treatment weeks | Temperature, °C. | | Daylight period, hours | Intensity of illumination, lux |
|---|---|---|---|---|
| | Day | Night | | |
| 1 | +10.0 | +5.0 | 9.5 | 14.0 |
| 2 | +8.0 | +4.0 | 9.0 | 11.0 |
| 3 | +6.0 | +3.0 | 9.0 | 10.0 |
| 4 | +4.5 | +1.5 | 8.75 | 9.0 |
| 5 | +3.5 | +0.5 | 8.75 | 8.0 |
| 6 | +3.0 | −3.0 | 21.00 | 15.0 |

It was observed that the plants reach their genetically determined maximum frost resistance after this wintering program.

The plants cultivated according to the above program were divided into two groups. Three parallel tests, extending to 5 cases each, were performed in each of the groups. The plants of both varieties belonging to the first group were treated at the end of the 4th and 5th weeks of the program with an aqueous spray solution according to the invention, containing 60 mmoles of active agent, by spraying them until dewiness. The plants of the second group served as untreated controls. At the end of the 6th week the plants of both groups were placed into a refrigerator equipped with a temperature programmer, and the temperature was lowered to −15° C. at a cooling rate of 2° C./hour. After 12 hours the plants were placed into a room of 0.5° C. temperature, maintained there for 0.5 hours, and then the conductivity of the leaves was measured. The conductivity data were applied to determine the surviving ability of the leaves.

In the conductometric measurements two needle electrodes were put into the leaves and conductivity was measured. Leaves not exposed to freezing (0% freezing) and leaves frozen in liquid nitrogen (100% freezing) were also tested as references.

This method enabled us to evaluate the survival of plants by an objective instrumental measurement beside the subjective bonitation method.

The resistace of the untreated and treated wheat plants to low temperatures is given in Table 4.

TABLE 4

| Wheat variety | Percentage survival after treatment at −15° C. |
|---|---|
| Miranovskaya 808, untreated | 85 |
| treated | 97 |
| Short Mexican, untreated | 8 |
| treated | 76 |

It appears from the data of the table that frost resistance improves even with the frost-resistant Miranovskaya 808 wheat variety (the percentage improvement is lower than with the other variety, which is obvious when considering their genetic characteristics), and with the frost-sensitive Short Mexican variety a very significant increase in survival can be observed, which reflects a substantial improvement in frost resistance.

EXAMPLE 10

Improvement of cold resistance has a particular importance in the cultivation of vegetable plants. One of the most serious problems in providing a uniform yearly vegetable supply is the risk of frost damages occurring when the plants are in their most sensitive development stage, which greatly influences the success of cultivation. Nowadays, under open air cultivation conditions, temperature is the decisive factor in the timing of planting or sowing and in the quality and quantity of crop yield.

As is known, cucumber is a plant requiring warm temperatures, it develops well at temperatures about 25° C., and its development stops completely below 18° C. Cucumber is very sensitive to temperature fluctuations, too, and it is completely destroyed by frost at temperatures below 0° C. It is well known that under early open-air cultivation conditions the seedlings, precultivated for about 6 weeks in hotbed or over manure under greenhouse conditions, can be planted out only in the middle of May, when the early spring frosts are over.

Tests were performed to determine how the cold resistance of cucumber can be influenced by treating it with a composition according to the invention.

Seeds of cucumber (Rhine bunch variety) were germinated for 3 days at 25° C., and 5 seedlings each were planted into 20 pots filled with a 1:1 mixture of sand and soil.

The pots were put into a greenhouse and the plants were cultivated for 21 days at 20°-25° C. and a relative humidity of 60%. Thereafter the plants were put for one day (illumination for 12 hours and darkness for 12 hours) into a climatizing chamber with a temperature of 8° C., and divided into two groups. In 10 of the pots the plants were sprayed with 5 ml of water per pot, whereas in the other 10 of the pots they were treated with 5 ml of a spray solution prepared by diluting the composition according to Example 6 with water to an active agent concentration of 30 mmoles.

The plants of both groups were maintained in a climatizing chamber for one day at 0° C., thereafter they were placed into a climatizing chamber of −2.5° C. temperature and maintained there in the dark for 16 hours. After this low-temperature treatment the plants were maintained at 25° C. for one day, and the recovery of plants was determined by bonitation.

All of the untreated plants were destroyed, whereas 90% of the plants treated with the composition according to the invention remained viable, i.e. they survived the damaging effects of low temperatures.

The lipoid composition of the plants was examined as described in Example 7. The results are listed in Table 5.

TABLE 5

| Type of phospho- | Amount of phospholipoids, nmole/leaf | |
|---|---|---|
| lipoids | Control | Treated |
| PA | 340.2 | 326.4 |
| PI | 100.7 | 205.3 |
| PC | 47.0 | 1115.2 |
| PE | 303.4 | 404.4 |
| PG | 121.7 | 630.5 |
| DPG | 254.7 | 713.9 |
| Total phospholipoids | 1167.7 | 3395.7 |

EXAMPLE 11

Green pepper is one of the most widespread cultivated vegetable plants in Hungary. It is known that green pepper, owing to its tropical origin, is rather sensitive to cold, and is frequently damaged by the early spring and, particularly, early autumn frosts.

Seeds of green pepper were germinated under laboratory conditions at 25° C., and the germinating seeds were planted into pots filled with a 1:1 mixture of sand and soil. The potted plants were cultivated for 2 months in a greenhouse at 20°-25° C. and a relative air humidity of 60%, by watering the pots up to 60% of the water capacity of the soil. A photoperiod of 14 hours was applied.

Thereafter, the plants were sprayed with aqueous solutions prepared from the composition described in Example 3, containing 0.02, 0.04 and 0.05% of active agent, respectively, and 24 hours later the plants were subjected to frost test.

In the frost test 100 mg of leaves, each, were removed from the treated plants and the untreated controls, the leaves were wrapped into aluminum foil, and placed into a metal block of programmable temperature so that the leaves were in direct contact with the metal walls of the block. Five parallel samples were taken for each of the tests.

The block was cooled from +10° C. to −5° C. at a cooling rate of 1° C./hour, and maintained at −5° C. for 3 hours. Thereafter, the block was re-heated to 0.5° C. at a heating rate of 1° C./hour, the leaves were removed from the block and subjected to conductometric examination.

The conductometric measurement method applied was elaborated by Dexter et al. [Dexter, S. T., Tottingham, W. E., Graber, L. F.: "Investigation of hardiness of plants by measurement of electrical conductivity", Plant Physiol. 7, 63–78 (1932)]. The essence of the method is that the plant or plant part to be examined is put into a prescribed amount of distilled water of known conductivity, and after a pre-determined period the conductivity of the electrolyte is measured. The increase in conductivity is due to the electrolytes released by the cells in water, and the release of electrolytes depends on the condition of the cells. In these measurements the leaves of untreated plants subjected to frost test (controls) showed the greatest conductivity, regarded as complete destruction (0% protection).

The lowest conductivity was observed with the leaves of untreated plants not subjected to frost test, regarded as complete (100%) protection.

Conductometric measurements were performed 60, 120, 180 and 240 minutes after putting the leaves into distilled water. Conductivity increased with the time, but remained constant after 240 minutes. These values, regarded as final, are listed in Table 6.

TABLE 6

| Active agent concentration | Protection, % |
|---|---|
| 0.00% (control) | 0.00 |
| 0.02 | 32.27 |
| 0.04 | 57.30 |
| 0.05 | 71.90 |

The test results show that green pepper, treated with an aqueous spray solution according to the invention containing 0.05% by weight of active agent, attained a 71.9% protection against the effects of −5° C. temperature.

EXAMPLE 12

Tests were performed with tomatoes which, like green pepper, are rather sensitive to cold.

Tomato, a plant accustomed to tropical climate, is very sensitive to temperature fluctuations. It is well known that prolonged temperature drops or night frosts damage the plants substantially, the damaged plants recovery only slowly, and this has an adverse effect on yield.

The tests were performed as described in Example 11 with the difference that tomato seeds were germinated and planted into pots. The seedlings were cultivated for one month, sprayed with an aqueous spray solution prepared from the composition described in Example 3 (active agent content: 2.1%), and frost test was performed then at −2.5° C. as described in Example 11.

According to the results of conductometric measurements the treatment provides a protection of 68.4%.

EXAMPLE 13

Under the climatic conditions of Hungary sowing of beans is timed so that the plants should emerge only after the frosts occurring almost every year at the beginning of May, in order to avoid the destruction of the young plants.

Bean seeds were germinated under laboratory conditions, the germinating seeds were planted into pots, and the plants were cultivated under greenhouse conditions as described in the previous examples. After the development of the second leaf pair the plants were treated with aqueous spray solutions prepared from the composition described in Example 3 (active agent content: 0.05% and 4.2% by weight, respectively).

Frost test and conductometric measurements were performed as described in Example 11 with the difference that the block was cooled to −2.5° C.

The results of the conductometric measurements indicate that a treatment with a spray solution of 0.5 w/w % active agent content provides a protection of 71.7%, whereas when treating the plants with a spray solution of 4.2 w/w % active agent content a protection of 90.9% can be attained.

EXAMPLE 14

It is known that spring frosts cause substantial damages, sometimes approaching 100%, in vine cultivation.

Tests were performed to determine how vine plants can be protected against frost with the compositions according to the invention.

Vinestalks were rooted under laboratory greenhouse conditions. When 2 or 3 leaves appeared on the stalks, the plants were sprayed with aqueous spray solutions prepared from the composition described in Example 6 (active agent content: 0.01, 0.02 and 0.04 w/w %, respectively). 24 hours after spraying the leaves were subjected to the frost test described in Example 11, by cooling the block to −5° C. The conductivity of the reheated leaves was measured as described in Example 11. The results are listed in Table 7.

TABLE 7

| Active agent content, % | Protection, % |
|---|---|
| 0.00 (control) | 0.00 |
| 0.01 | 65.30 |
| 0.02 | 83.80 |
| 0.04 | 86.60 |

EXAMPLE 15

Spring frosts frequently cause substantial damages in fruit orchards. Bursting buds and flowers become damaged upon prolonged temperature drop or temperatures below 0° C., the flowers fall, and no crop develops.

Apricot branches cut off before flowering were applied in the tests. The buds on the branches were counted.

Some of the branches were not treated, whereas the majority of the branches were sprayed with an aqueous spray solution prepared from the composition described in Example 6 (active agent content: 4.2%). 24 hours after spraying all branches were put into a climatizing chamber, the temperature of the chamber was lowered to −2.5° C., and the branches were maintained for 3 hours at this temperature. Thereafter the temperature of the chamber was raised to room temperature again, the branches were removed, placed into a greenhouse, and flowering was investigated. Flowering occurred 2–3 days after this treatment. The branches which lost the flowers after flowering were regarded as frost-bitten.

With the untreated branches 98 of 100 bursted buds were lost, whereas with the treated branches only 26 of 100 bursted buds fell and the others flowered strongly. This means that the treatment resulted in a protection of 74%.

EXAMPLE 16

It is known that of the ornamental plants carnations are sensitive to temperatures around 0° C.

Carnation plants cultivated in cases were sprayed with an aqueous solution prepared from the composition described in Example 3 (active agent content: 4.0% by weight), and 24 hours later the plants were subjected to frost test.

The cases with treated and untreated plants were put into a climatizing chamber cooled to −2.5° C., the plants were maintained for 3 hours at this temperature, and then the temperature of the chamber was re-set to room temperature. The buds blackened on all of the untreated plants and fell later, and the mother plants were destroyed, too.

On the other hand, with the treated plants only 35 of 100 buds fell down, and flowers developed from 65 buds. This means that a protection of 65% was attained.

EXAMPLE 17

Tests were performed to determine whether a treatment with a composition according to the invention is also able to protect plants cultivated under nearly tropic climates from frost damages.

The tests were performed on coffee-tree branches with leaves of the same age, obtained from the botanic garden of the József Attila University of Sciences, Szeged (Hungary).

The branches were put into aqueous solutions of the composition described in Example 6 (active agent content: 0.4, 2.1 and 4.2% by weight, respectively) for 24 hours at room temperature. Thereafter the treated and untreated branches were placed into a climatizing chamber thermostated to +0.5° C. The branches were maintained in the chamber for 0.5, 3, 6, 9 and 18 hours. Leaves were removed from the branches, and the conductivity of the leaves was measured as described in Example 11. The conductivity of the leaves removed from the untreated branches increased abruptly in parallel with the increase of the residence time in the climatizing chamber. After 6 hours of climatizing brown spots, indicating necrosis, appeared on the leaves of the untreated branches, and the number of brown spots increased with the time of climatization.

Similar phenomena, but with a delay, were observed on the leaves of the branches treated with an aqueous solution of 0.5% active agent content, too. On the other hand, the leaves of the branches treated with aqueous solutions of 2.1% and 4.2% active agent contents remained fresh over the whole test period, and no deterioration or necrosis could be observed on them when maintaining the branches at room temperature after climatization. The conductivity of the leaves removed from the branches after different residence times in the climatizing chamber was practically unchanged.

This shows that the branches treated with aqueous solutions of 2.1% and 4.2% active agent content were protected almost completely, whereas the untreated ones were unable to tolerate the effects of 0.5° C. temperature.

According to the conductivity measurements the protection of the branches treated with aqueous solutions of 0.5, 2.1 and 4.2 w/w % active agent contents, respectively, was 72.5%, 93.3% and 97.4% after climatizing them for 6 hours.

The results of the tests listed in Examples 7 to 17 demonstrate that the treatments performed with the compositions according to the invention provide a substantial increase in cold resistance, and thus a significant protection against frost damages, on a wide range of cultivated plants. This protection has a substantial role in agriculture for ensuring crop yield security.

The compounds of the formula (I) are known compounds. As a literature source describing them and their preparation, respectively, e.g. the following ones can be cited:

(a) Houben-Weyl: "Methoden der organischen Chemie" 4. völlig neugestaltete Auflage (1958)
volume 6/1a, p. 412 to 416
volume 11/2, p. 599
volume 11/2, p. 610

(b) Kirk-Othmer: "Encyclopedia of Chemical Technology", third edition, volume 6, p. 19 to 28 (1979)

(c) Sebrell and Harris: "The Vitamins", volume 3, p. 436 to 437 (1971), Academia Press, New York

What we claim is:

1. A method for increasing the cold resistance of a cultivated plant, which comprises the step of treating the cultivated plant before a temperature drop with an aqueous solution of a composition containing as active ingredient 0.001 to 5.000% by weight of at least one compound of the formula I

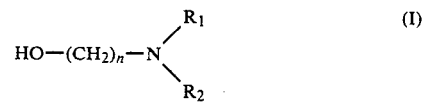

wherein n is an integer of 2 to 5 and $R_1$ and $R_2$ each stand for hydrogen or an N,N,N-trimethyl-quaternary ammonium salt thereof.

2. The method defined in claim 1, wherein seedlings or roots are treated before the temperature drop with an aqueous solution of the composition containing 0.01 to 2.00% by weight of active ingredient.

3. The method defined in claim 1, wherein leaves, sprouts or flowers are sprayed before the temperature drop with an aqueous solution of the composition containing 0.01 to 4.50% by weight of active ingredient.

4. The method defined in claim 1, wherein branches or crops are treated before the temperature drop by soaking or dipping them in an aqueous solution of the composition containing 0.5 to 5.0% by weight of active ingredient.

5. The method defined in claim 1, wherein the active ingredient of the formula I is 2-hydroxyethylamine.

6. The method defined in claim 1, wherein the active ingredient of the formula I is trimethyl-beta-hydroxyethyl-ammonium chloride.

7. The method defined in claim 1, wherein the active ingredient is a mixture of a compound of the formula I and a quaternary ammonium salt thereof.

8. The method defined in claim 7 wherein the active ingredient is a mixture of 2-hydroxyethylamine and trimethyl-beta-hydroxyethyl-ammonium chloride.

9. The method defined in claim 8 wherein the active ingredient contains 2-3 parts of the 2-hydroxyethylamine to 3 parts of the trimethyl-beta-hydroxyethyl-ammonium chloride.

* * * * *